United States Patent [19]

Ciavattoni et al.

[11] 4,125,774
[45] Nov. 14, 1978

[54] PANORAMIC DENTAL X-RAY MACHINE

[75] Inventors: Anthony Ciavattoni, Staten Island, N.Y.; Josef Ujvary, Kingston; John M. Gardella, Matawan, both of N.J.

[73] Assignee: Pennwalt Corporation, Philadelphia, Pa.

[21] Appl. No.: 856,422

[22] Filed: Dec. 1, 1977

[51] Int. Cl.² ............................................. G03B 41/16
[52] U.S. Cl. ............................ 250/439 P; 250/445 R; 250/449
[58] Field of Search ............... 250/439 R, 439 P, 444, 250/445 R, 446, 447, 448, 449, 451, 490

[56] References Cited

U.S. PATENT DOCUMENTS

| 2,798,958 | 7/1957 | Hudson | 250/439 P |
| 3,045,118 | 7/1962 | Hollman | 250/439 P |
| 3,906,227 | 9/1975 | Ensslen | 250/439 P |

Primary Examiner—Craig E. Church

[57] ABSTRACT

A dental X-ray machine for providing both continuous and discontinuous radiographic images of a patient's dental arch area. Continuous images are obtained when an X-ray source-camera assembly orbits a patient in one direction while the patient is transported in a substantially semicircular pattern in the opposite direction. The pattern is achieved through improved X-Y drive mechanism which rotates a crank assembly having a pair of depending roller guides, one of which roller guides engages guideway means affixed to a plate which is capable of traveling in an X-direction only, and the other roller guide engaging similar guideway means affixed to another plate which is capable of traveling in a Y direction only. The combined motion of the plates, upon rotation of the crank assembly produces an X-Y pattern resembling a semicircle. Discontinuous images are obtained when another plate, which plate also guides the aforementioned plate capable of moving in the X direction only, is shifted in the Y direction by a cam-drive rod mechanism when the patient's spinal cord becomes aligned with the X-ray source-camera assembly.

13 Claims, 14 Drawing Figures

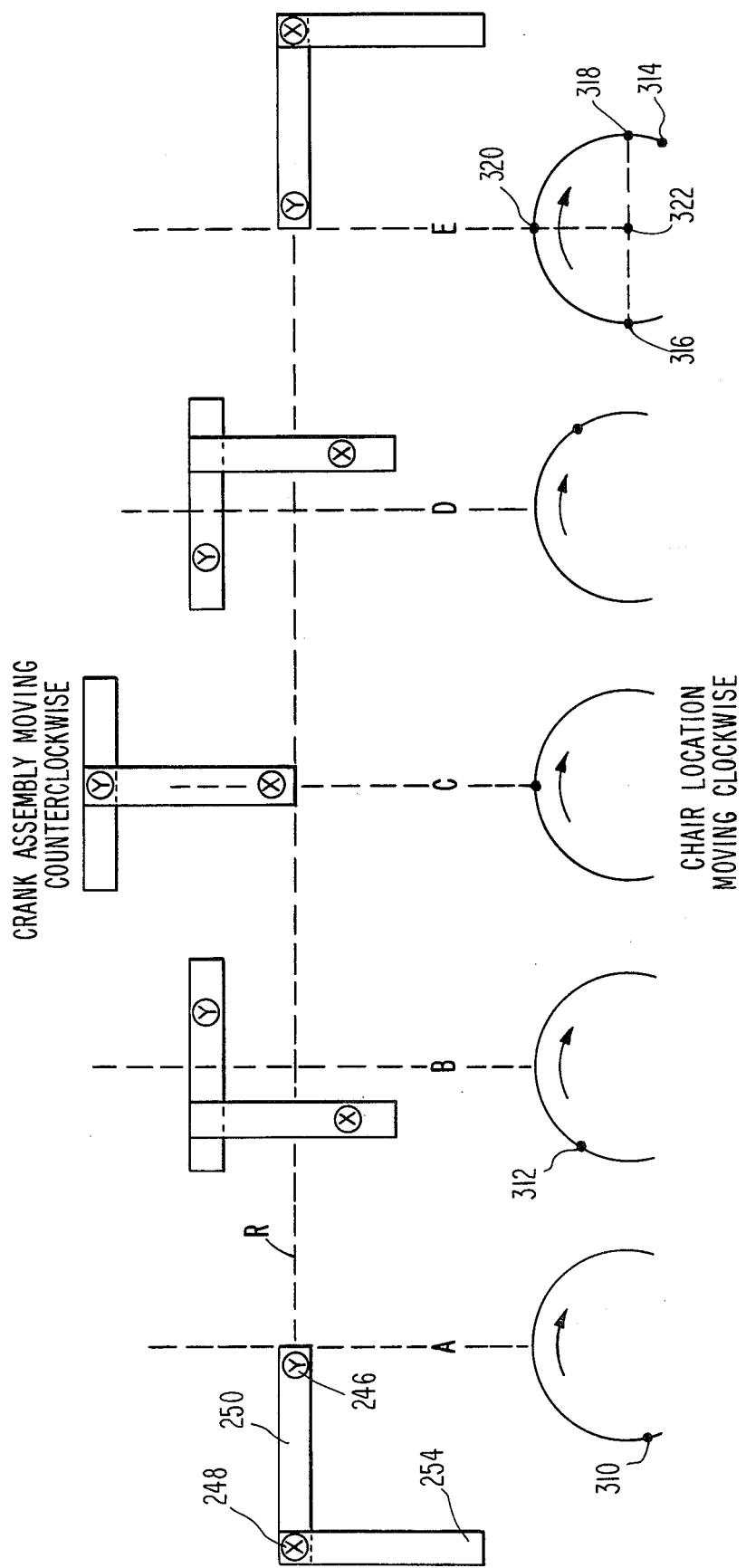

PANORAMIC DENTAL X-RAY MACHINE

CROSS-REFERENCE TO OTHER RELATED APPLICATIONS

Reference is hereby made to copending patent application, Ser. No. 856,423, filed Dec. 1, 1977, for "Excursion Mechanism for Panoramic Dental X-Ray Machine" of A. Ciavattoni et al., assigned to the same assignee hereof.

STATEMENT OF THE INVENTION

The present invention relates to X-ray apparatus and more particularly concerns a chair shift mechanism and an X-Y drive mechanism for transporting a patient chair in accordance with patterns which will provide both continuous and discontinuous panoramic radiographs of dental arch and temporomandibular joint areas.

BACKGROUND OF THE INVENTION

Prior art panoramic dental X-ray apparatus are well known in the art. Some provide a continuous image of the dental arch area and commonly employ an X-ray source and X-ray film supported on a rotatable carrying arm which orbits a patient situated in the beam path. The patient may remain stationary in the chair or be transported in accordance with various X-Y type drive mechanisms in order to simulate the generally elliptical shape of the human dental arch. The continuous image radiograph provides the dentist with a panoramic view of the teeth and associated structures and is a useful diagnostic aid in many phases of dental practice.

Various other prior art apparatus provide a discontinuous, or split image panoramic radiograph which possesses certain advantages. Here, the dentist is provided with additional interpretive information since two distinctly different views of the incisors, or centrals area are provided. For example, consider the split image radiograph as two separate films. A pathology located on the left half is noted with respect to its relationship to the centrals, or incisors. The same pathology is located on the right half. If the image of the pathology, such as an impacted canine, appears to move away from the patient's midline, the pathology is palatally located. Conversely, if the image of the pathology moves toward the midline, it is labially located. Additionally, overlying spinal shadows which would be cast over the central-bicuspid region are eliminated since X-rays are not generated when the spine is aligned with the X-ray source and film.

BRIEF DESCRIPTION OF THE DRAWINGS

FIG. 14 is a diagrammatic representation illustrating dependence of chair location on crank assembly position.

DETAILED DESCRIPTION OF THE INVENTION

Figure 1:
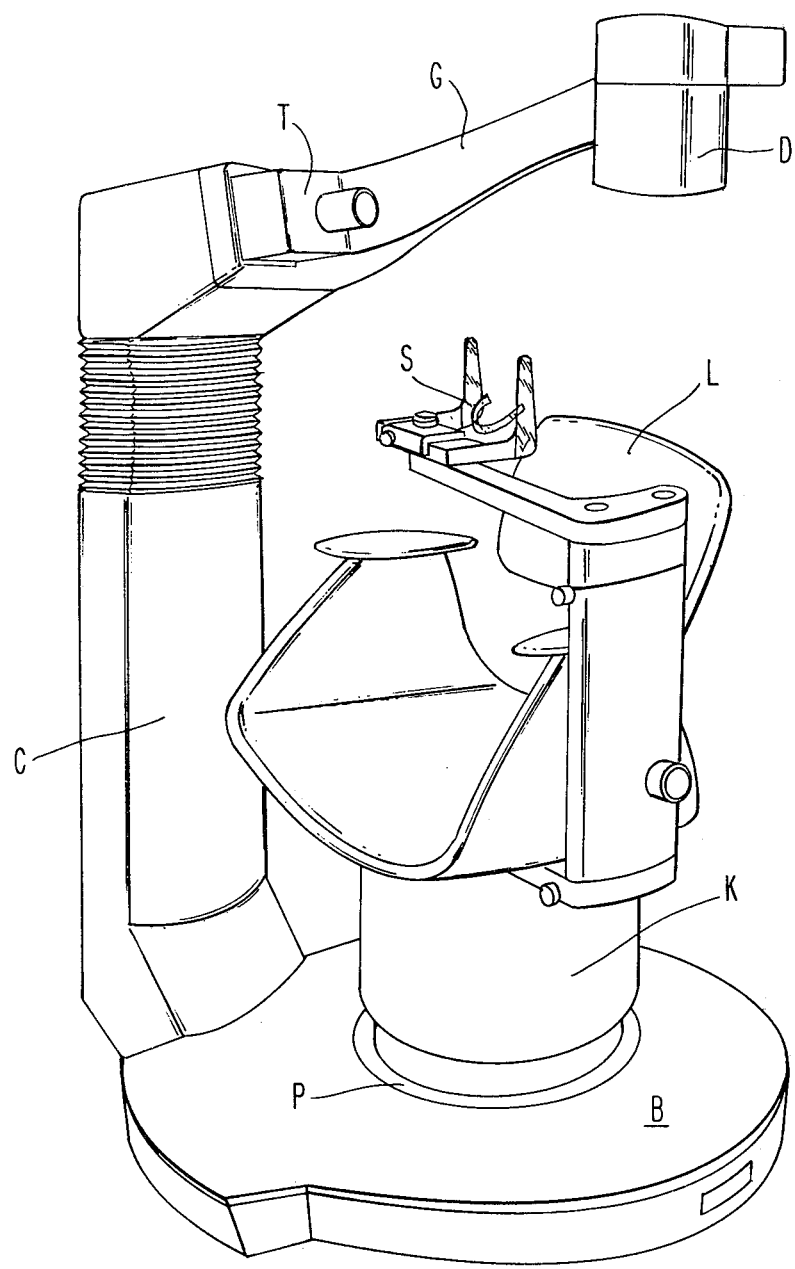
FIG. 1 is a perspective view of dental X-ray apparatus embodying the invention.

Referring to FIG. 1 of the drawings, the panoramic X-ray machine comprises a base B having a stationary platform P disposed generally centrally thereof. Platform P supports a patient chair L including means S for supporting the chin and head of a patient. A column C is caused to rotate around chair L, the column carrying a tubehead T, a camera supporting arm G, and a camera D which includes the usual film holding means. The X-Y drive mechanism is located below chair L, within shroud K, the mechanism being bolted securely to stationary platform P. The mechanism for causing column C to rotate around stationary platform P is supported and partially housed in base B, and is hereinafter referred to as the excursion mechanism.

An X-Y drive mechanism is capable of transporting a patient chair in the X direction (front to back) or Y direction (side to side) or in a combination of X and Y directions, i.e., any direction in the XY plane. Because the present invention concerns an X-Y drive mechanism which cooperates with an orbiting column including an X-ray source and camera, a description of the excursion mechanism which causes the column to orbit follows.

As described in cross-referenced copending application of Ciavattoni et al., column C orbits the patient in a circular pattern. Since the average dental arch however is somewhat elliptical or semicircular, a patient must be transported in the patient chair by means of mechanism which will develop a pattern to provide an overall net movement of both patient chair and column rotation which will maintain the distances to each tooth from the X-ray source practically constant and thus permit sharp images of the entire dental arch and temporomandibular joint areas.

The mechanism must not only be capable of producing the necessary movement pattern to the patient chair in order to provide the continuous panoramic radiographs as just described, but must also, through switching means to be described hereinafter, be capable of coacting with the excursion mechanism to provide the discontinuous, or split panoramic images.

Figure 2:
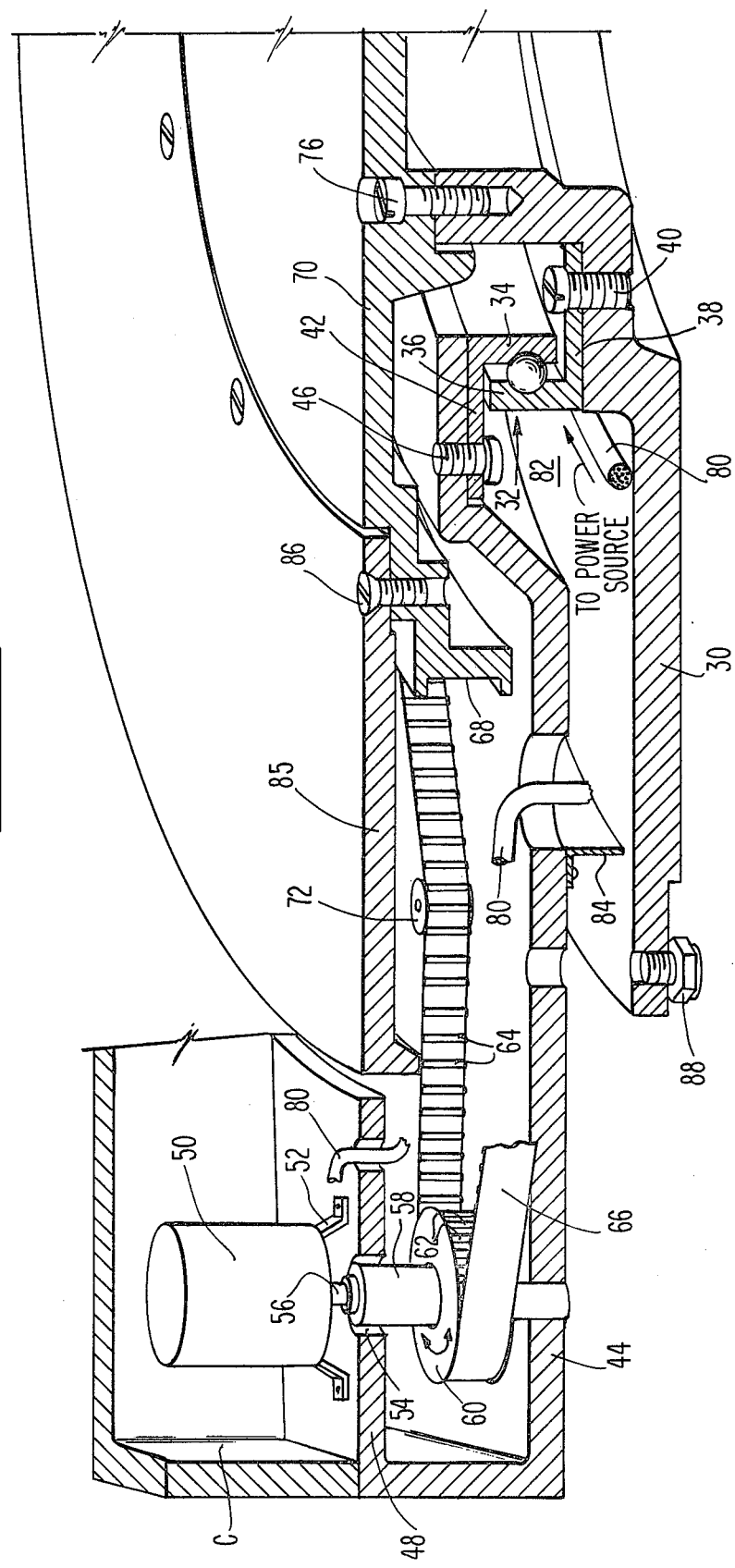
FIG. 2 is a cutaway perspective view of a portion of the base and excursion mechanism of the embodiment shown in FIG. 1.

Referring now to FIG. 2, a base plate 30, preferably an aluminum casting, carries a circular flange mounted bearing 32 having an inner race 34 and an outer race 36. Outer race 36 includes a lower flange 38 which is secured to base plate 30 by circumferentially spaced screws 40. Similarly, upper flange 42 of inner race 34 carries rotating disc 44. Upper flange 42 and rotating disc 44 rotate as a unit and are held together by means of circumferentially spaced shoulder screws 46.

Rotating disc 44 carries column C which is provided with a horizontal plate member 48, upon which is mounted a synchronous step motor 50 by means of brackets 52. An opening 54 is provided in horizontal plate 48 through which shaft 56 of motor 50 communicates with a conventional electromagnetic slip clutch 58. Clutch 58 serves to couple shaft 56 with sprocket 60 which is rotatably mounted to rotating disc 44. Sprocket 60 is provided with teeth 62 which coact with spaced projections 64 on a belt 66. The belt is accommodated within an annulus 68 provided around stationary platform P which supports the patient chair L.

It should be emphasized that belt 66 does not rotate around platform P. Belt 66 is held immovable against annulus 68 at that portion of the annulus farthest removed from sprocket 60 by means to be described more fully hereafter. To further clarify, any given point on belt 66, such as point E, for example, will always contact a specified point, and no other point, on annulus 68, such as point F, regardless of the direction of limited rotation of rotating disc 44. Belt 66 provides the means therefore for translating the rotation of sprocket 60 into limited orbital rotation of rotating disc 44 and column 18.

A flexible electric cable 80 passes up through column C for connecting the power source to the X-ray source and camera, and to the motor (not shown) which elevates or lowers the tubehead assembly in column C. The cable is also connected to motor 50, slip clutch 58, and a microswitch assembly to be described hereinafter. In order to insure unimpeded vertical movement of the tubehead assembly and the orbiting of column C, cable 80 will be provided with a sufficient length. To that end, a space 82 is provided above base plate 30 to permit coiling and uncoiling of cable 80 during movement of the tubehead and column. A cable control band 84 is mounted to an underside portion of rotating disc 44 for restricting cable 80 within space 82.

A removable cover plate or step plate 85, suitably an aluminum casting, protects the excursion mechanism as well as affording means upon which the patient may step and rest his feet. Step plate 85 is removably attached to stationary platform P by screws 86. Leveling screws 88 are provided in base plate 30.

Figure 3:
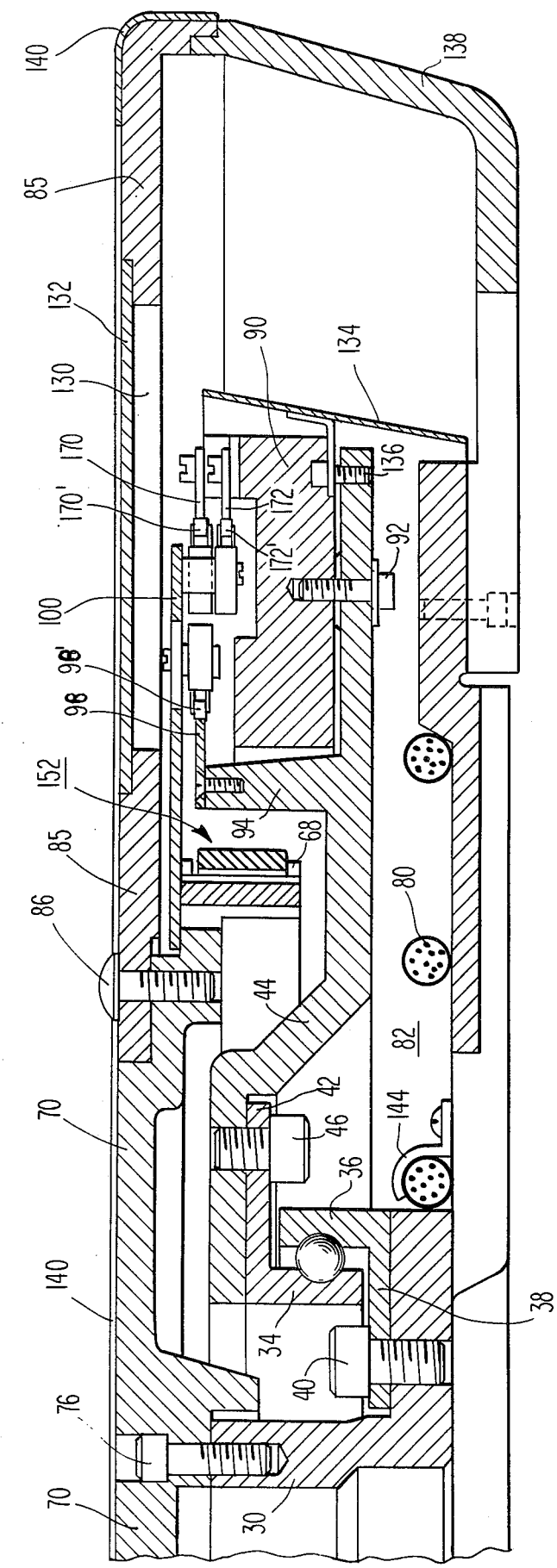
FIG. 3 is a sectional view of another portion of the base and excursion mechanism.
Figure 4:
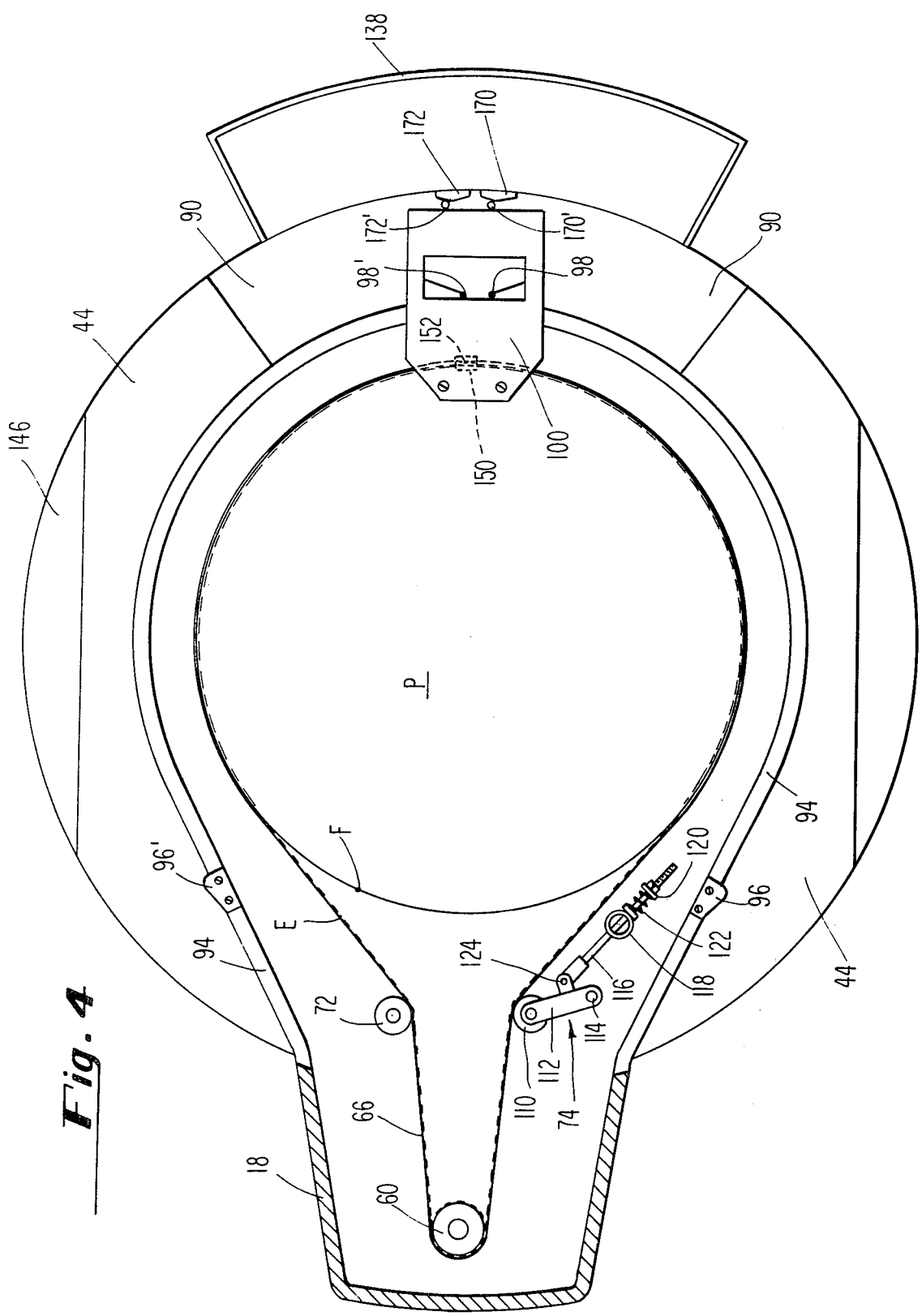
FIG. 4 is a plan view, partially in section, of the excursion mechanism with portions removed for clarity.

For a better understanding of the invention, reference should now be made to FIGS. 3 and 4 wherein a balancing weight 90, suitably cast iron, is shown seated on an outer portion of rotating disc 44, the weight 90 being positioned in counterbalancing relation to column C. Screws 92 maintain balance weight 90 in a fixed position on rotating disc 44. An annular ring 94 upstands from rotating disc 44 and carries a pair of cams 96 and 96' which respectively actuate microswitches 98 and 98' to limit the total excursion of rotating disc 44 to about 240°. Microswitches 98 and 98' are carried on a switch plate 100 mounted on stationary platform P. More specifically, when rotating disc 44 moves in a counter-clockwise direction, switch 98 will be actuated by cam 96 to open the circuit to motor 50. Conversely, can 96' actuates limit switch 98' when rotating disc 44 moves in a clockwise direction to open the circuit to motor 50. Cams 96 and 96' are so positioned that column C and rotating disc 44 are permitted only about 240° of rotation in either direction. Circuitry for the cam-microswitch arrangement is conventional and are not detailed herein.

Adjustable idler pulley assembly 74 comprises an idler wheel 110 rotatable on arm 112 which is pivotally mounted to rotating disc 44 by screw 114. A holder 116 is slidably insertable through a nut 118 which is fixedly secured to rotating disc 44. Thus, idler wheel 110 will be displaced inwardly to increase tension on belt 66 when screw 120 is tightened against compression spring 122 to cause arm 112 to pivot clockwise on screw 114 by means of pivot pin 124.

Step plate 85 is provided with a recess 130 for receiving a removable access plate 132 for easy access to switch plate 100.

A skirt 134 extends around rotating disc 44 and is mounted thereto by screws 136 while a step plate support member 138 is bolted to base plate 30. A step plate cover 140, preferably rubber or vinyl, is fitted over the step plate.

A clamp 144 may be employed to secure cable 80 against base plate 30.

Rotating disc 44 may be provided with removable wings 146 to enable passage of the X-ray machine through restricted openings.

Figure 5:
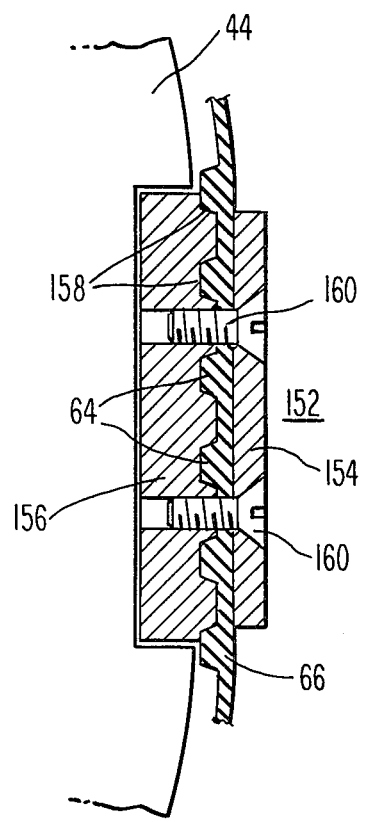
FIG. 5 is a sectional view of the belt-fastening means used in the excursion mechanism.

Annulus 68 of stationary platform P has a cut-out area, or notched recess 150 for receiving a belt-fastening assembly 152 therewithin (FIG. 5) comprising an outer plate 154 and an inner plate 156 which includes grooves 158 for accepting projections 64 of belt 66. The plates 154 and 156 are secured together by screws 160.

In the operation of the excursion mechanism, any rotary motion of shaft 56 of motor 50 will not be coupled to sprocket 60 until sufficient voltage is supplied to the coils of clutch 58. That is, the clutch will be permitted to "clip" until actuated. However, once actuated by a sufficient voltage, rotation of sprocket 60 will be effected. Since belt 66 is held fast against annulus 68 in the vicinity where belt-fastening assembly 152 engages notched recess 150 provided in stationary platform P, rotation of the sprocket causes column C and rotating disc 44 to orbit around the stationary patient platform. Thus, belt 66 will translate the rotational movement of sprocket 60 into a clockwise or counterclockwise excursion of the column depending upon the direction of rotation of the sprocket. More specifically, rotation of sprocket 60 in a clockwise direction causes column C and rotating disc 44 to orbit in an opposite direction, and vice-versa.

Reversing the direction of rotation of shaft 56 of motor 50, and circuitry supplying the necessary voltage to actuate slip clutch 58 is well known. For the purposes of this invention, step motor 50 is geared down by conventional means to permit 1.83 rpm of the column and rotating disc.

Figure 6:
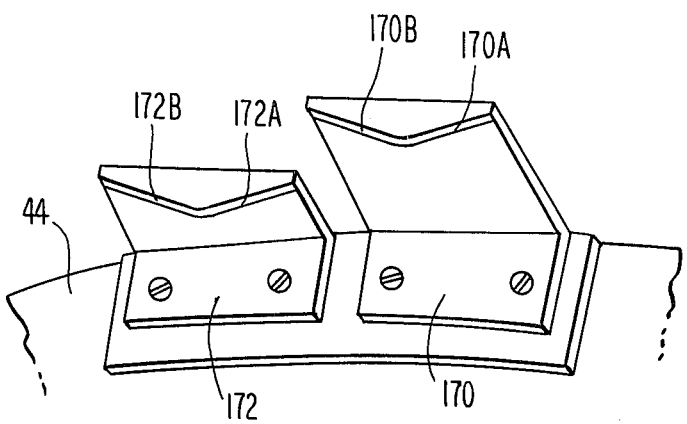
FIG. 6 is a perspective view of the cam arrangement for providing a split image panoramic radiograph.

Since, as aforementioned, the present invention contemplates a chair shift mechanism and an X-Y drive mechanism, features well-known in the art which are essential to the operation of a panoramic dental X-ray machine are not described herein. For example, it is well known that as column C is rotated about a patient means must be provided to accomplish an independent movement of the X-ray film in order to achieve proper exposure of the film. The movement must be in a particular time sequence with respect to the rotation of column C, but as such mechanism forms no part of the present invention, none will be described, and the apparatus to accomplish this has been omitted from the drawings for the purposes of simplification. However, the cam and microswitch means for effectuating interruption of both film travel and generation of X-rays is not only essential, but cooperates with the present chair shift mechanism for providing the discontinuous panoramic images. Thus, reference is made to FIG. 6 wherein cams 170 and 172 are mounted to rotating disc 44 to respectively actuate switches 170' and 172' (FIGS. 3 and 4), adjustably mounted on switch plate 100. Switches 170' and 172' are connected to the X-ray source and film drive respectively. As rotating disc 44 rotates counterclockwise, for example, switches 170' and 172' will ride on cam surfaces 170A and 172A respectively to open the circuits to the X-ray source and film drive, but not simultaneously. In order to provide images free of distortion, it is desirable that the film continue to travel for an instant or so after shutting off the X-ray source, for reasons to follow. In a discontinuous, or split image panoramic radiograph, X-rays are not generated when the spine is aligned with the X-ray source and X-ray film, resulting in a radiograph having a distinctive white band between the centrals. Such a white band approximately 1 inch wide, would result if the X-ray film was allowed to travel during the entire period the X-rays were not being generated, i.e., when traversing the spine. On the other hand, a one inch wide band is considered objectionable by many dentists since it is not only wasteful of valuable space on the radiograph, but tends to hinder diagnosis by the dentist. For discontinuous or split panoramic images, image distortion of the centrals would result if the white band were eliminated. It should be mentioned herein that discontinuous panoramic images require the establishment of two pivot points, one each behind the left and right molar areas. Essentially, true image portrayal is thus achieved because the distance from an X-ray pivot point to any tooth to be X-rayed from that pivot point is practically constant. That is, after one-half the dental arch is X-rayed, the center of rotation to the other pivot point is effected by a chair shift, mechanism for which is later described in detail. In order to prevent image distortion which would result if an attempt were made to superimpose the images of the centrals, a white band of proper width, approximately ¼ inch, provides a true perspective image of the centrals as well as separate views for increasing the interpretive capabilities by the dentist.

In accordance with the above, switch 170', connected to the X-ray source, will be opened by cam surface 170A to stop any further generation of X-rays by the X-ray source. Immediately thereafter, switch 172' opens the circuit to suitable film drive mechanism to stop film travel. Upon continued counterclockwise movement of rotating disc 44, switch 172' contacts cam surface 172B to close the circuit to the film drive to start the travel of the film again. Switch 170' is then immediately actuated by cam surface 170B to close the circuit to the X-ray source to start the flow of X-rays once more. Thus, the sequence of operation of the X-ray source and film drive is: X-rays off; film stopped; film started; X-rays on. In the embodiment described, power to the X-ray source is removed for about 2 seconds.

Regardless of the direction of rotation of rotating disc 44, power to the X-ray source will be cut off before film travel is stopped. Power will be returned to the X-ray source immediately after the film has again started to travel. To further clarify, assume rotating disc 44 is rotating in a clockwise direction. Since switch 170' was last actuated by cam surface 170B which returned the switch to its normally closed position while the rotating disc was then rotating counterclockwise, switch 170' will now be opened by cam surface 170B to cut off power to the X-ray source. Film travel will then be stopped; and started, prior to the regeneration of X-rays. By adjusting the position of switches 170' and 172' on switch plate 100, the width of the white band can readily be controlled. Thus, a narrow white band is readily achieved by means of the cam-switch arrangement for adjustably controlling the amount of film travel after the X-ray source has been rendered inactive.

Cams 170 and 172 have cam surfaces which are not coplanar. Similarly, switches 170' and 172' are mounted in non-coplanar relationship on switch plate 100 (FIG. 3). Because of this arrangement, switch 170' will only be actuated by cam 170 while cam 172 will only actuate switch 172'.

Figure 7:
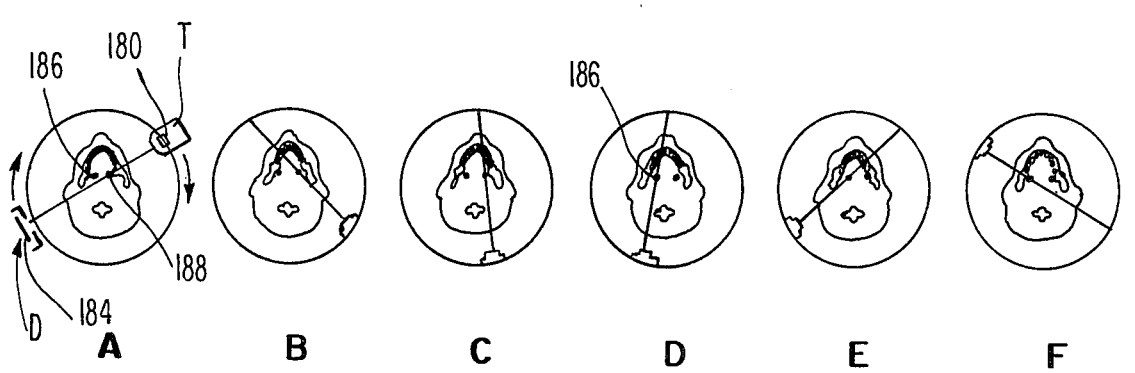
FIG. 7 is a diagrammatic representation depicting progressive steps in making a discontinuous panoramic radiograph.

In further clarification of the above, reference is made to FIG. 7 wherein tubehead T includes an X-ray source 180 for activating X-ray film 184 contained within camera D. A pair of pivot points 186 and 188 are selected behind the left and right molar areas respectively which serve as imaginary axes for rotating the tubehead-camera assembly.

In diagrams A, B, and C, pivot point 188 is used as the axis of rotation for radiographing the left half of the dental arch-temporomandibular joint area of the patient. When the tubehead-camera assembly reaches the position shown in diagram C, the patient chair is shifted to the right by chair shift mechanism, later described, in order that the axis of rotation of the tubehead-camera assembly coincides with pivot point 186 (diagram D) for radiographing the right half dental arch-temporomandibular joint area.

It should be emphasized that orbiting of the tubehead-camera assembly about the patient is not interrupted while the chair is shifting (between diagrams C and D) but that power to the X-ray source and film drive is shut off as previously described. More specifically, the film drive cut-off is effected by cam 172 opening switch 172', which also closes the circuit to the motor in the chair shift mechanism to thereby shift the chair. Circuitry between the motor and switch 172' is conventional and is not described or shown in the drawings.

Diagrams C and D reveal that two distinctly different views of the centrals, or incisors, is provided by the discontinuous, or split image panoramic radiograph made in accordance with the above. The images are sharply focused and possess a "forgiving" focal trough, i.e., one which readily accommodates a variety of dental arch sizes and asymmetry.

The tubehead-camera may be rotated in a counter-clockwise direction in which case the chair will be shifted to the right. Circuitry is conventional and is not shown.

Figure 8:
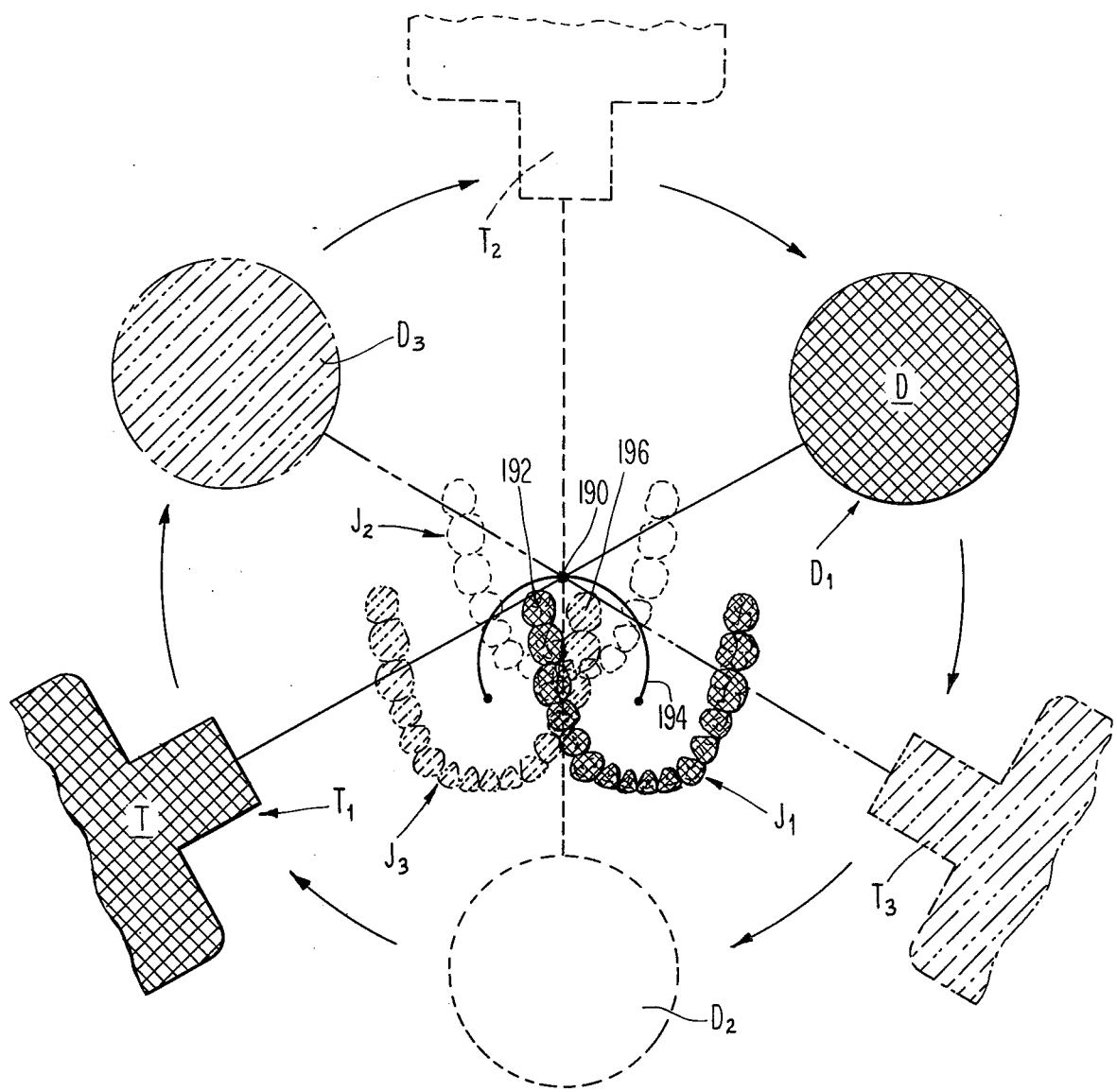
FIG. 8 is a diagrammatic view showing various positions of tubehead-camera assembly and dentition in making a continuous panoramic radiograph.

In the continuous mode of operation, the tubehead-camera assembly is rotating continuously in one direction for about 240° while the patient chair is simultaneously being transported continuously in the other direction in a substantially semicircular pattern as depicted in FIG. 8 wherein tubehead T contains an X-ray source therein which activates X-ray film contained within camera D, the tubehead and camera rotating as a unit or assembly around the patient about an imaginary axis 190. Selected positions of the tubehead, camera, and patient's dentition are indicated $T_1$, $T_2$, and $T_3$; $D_1$, $D_2$, and $D_3$; and $J_1$, $J_2$, and $J_3$ respectively. For purposes of clarity, the tubehead, camera, and dentition $J_1$ are marked with a criss-cross pattern to indicate the relative positioning of $T_1$-$D_1$-$J_1$. The $T_2$-$D_2$-$J_2$ relative positioning is indicated by dotted lines, while hatched lines illustrate the relative positions of the tubehead, camera, and dentition at $T_3$-$D_3$-$J_3$.

With the patient seated in the patient chair L (facing the reader), the upper right molar 192 of dentition $J_1$ is X-rayed by tubehead-camera assembly $T_1$-$D_1$. As the assembly starts its clockwise rotation, the chair is transported in a counterclockwise direction in a small semicircular-like pattern 194, through X-Y drive mechanism to be described hereinafter. Thus, when the tubehead-camera assembly has reached position $T_2$-$D_2$, the patient will have been transported to dentition position $J_2$ at which point of time and travel, approximately one-half of the dental arch-temporomandibular joint area will have been X-rayed. Upon further clockwise rotation of the tubehead-camera assembly to point $T_3$-$D_3$, the dentition will have assumed position $J_3$, and the upper left molar 196 of dentition $J_3$ will have been X-rayed to thus complete the necessary radiographing of the patient. The X-ray machine herein disclosed is capable of transporting a patient in either direction, i.e., in a counterclockwise direction as indicated by pattern 194, or in a clockwise direction, both by means of the present X-Y drive mechanism. The tubehead-camera assembly however will orbit about the patient on axis 190 in a direction opposing the direction of movement of the chair.

Figure 9:
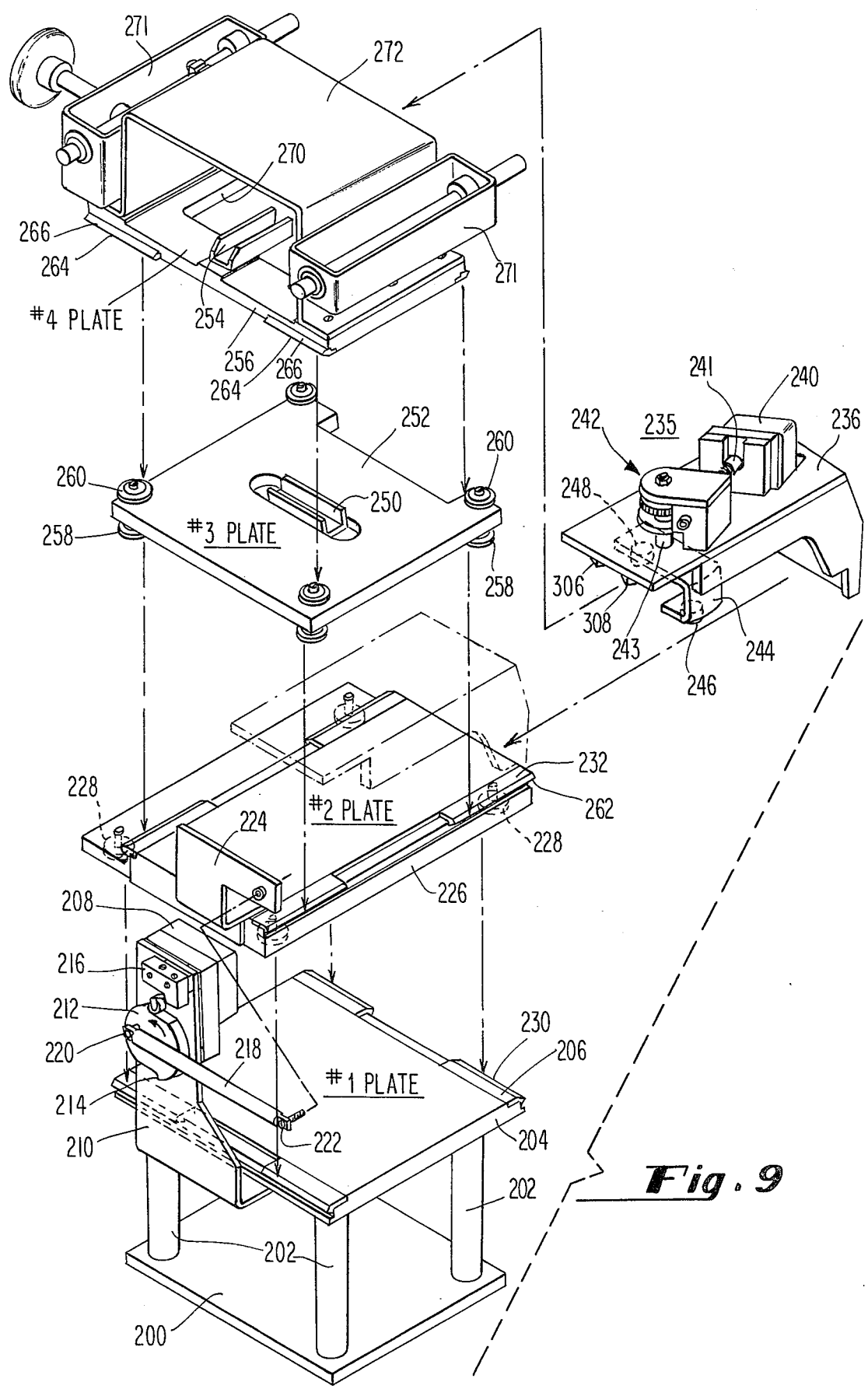
FIG. 9 is an exploded perspective view of the chair shift mechanism and X-Y drive mechanism of the invention.
Figure 10:
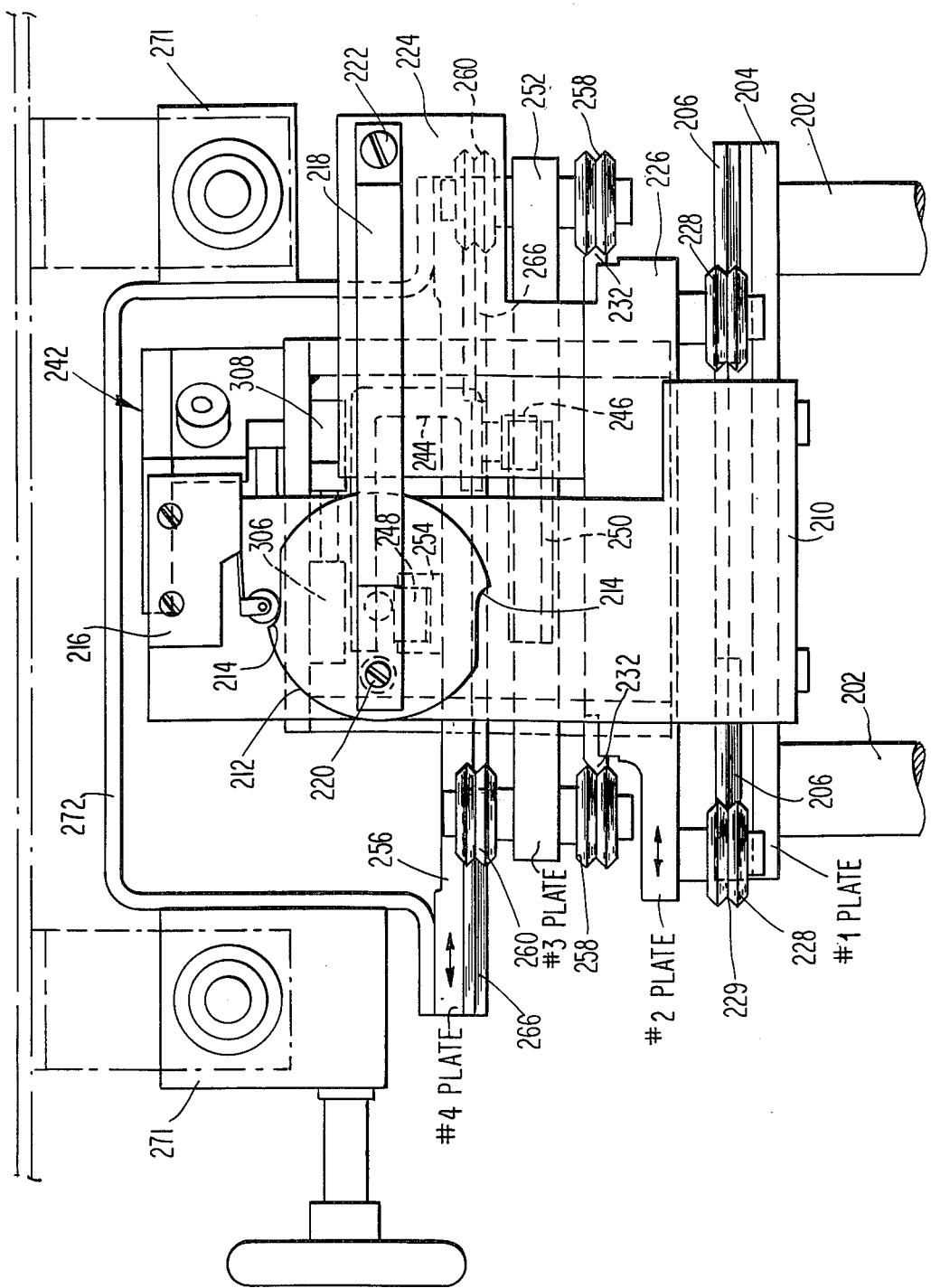
FIG. 10 is a front view of FIG. 9, assembled, with parts omitted for clarity.

Referring now to FIGS. 9 and 10, base 200 is rigidly affixed to stationary platform P by means well known and carries legs 202 which support bottom plate 204 hereinafter referred to as plate No. 1, or No. 1 plate. Plate No. 1 is provided with a pair of spaced parallel hardened ways 206 which are oriented along the Y-axis, that is, from side to side. Ways 206 provide the means for shifting chair L when discontinuous, or split panoramic images are desired and are not used when making continuous images. A motor 208 is mounted on bracket 210 which is mounted on plate No. 1. Motor 208, referred to as the chair shift motor, is self-braking, shaded pole, nonreversible, A.C., and has a 16 rpm output shaft connected to cam disk 212. The cam disk is symmetrical, shown in FIG. 10, having a pair of opposed lobes 214 disposed 180° apart, which contact microswitch assembly 216 to open or close the circuit to chair shift motor 208. A chair shift, for split images, takes almost two seconds to complete its travel of approximately 1¾ inch.

Electrical connections between microswitch assembly 216 and chair shift motor 208 are conventional and do not appear in the drawings.

A drive rod 218 has one of its ends 220 pivotally, off-centrally connected to cam disk 212, while its other end 222 is connected to arm 224, mounted on plate 226, hereinafter referred to as plate No. 2, or No. 2 plate. Thus, when chair shift motor 208 causes chair L to shift upon rotation of cam disk 212, shown counterclockwise, end 220 of drive rod 218 is caused to pivot about its pivot point to urge arm 224 and plate No. 2 to the right. Of course, it should be appreciated that chair L will alternately shift directions each time cam disk 212 rotates an additional 180. Plate No. 2 is provided with ball bearing mounted hardened wheels 228 which are peripherally recessed at 229, or V-shaped, for receiving and rolling along horizontally disposed knife-edges 230 of hardened ways 206 of plate No. 1. Plate No. 2 is also provided with a pair of spaced parallel hardened ways 232, oriented along the X-axis, or normal to ways 206.

Secured to plate No. 2 is an X-Y drive motor assembly 235 comprising an X-Y drive motor mount 236 which supports X-Y drive motor 240. Motor 240 is synchronous, A.C., reversible, having a 60 rpm output shaft 241 connected to gear reducing mechanism 242, later described, which results in geared down shaft 243 having 1½ rpm. Shaft 243 rotates crank assembly 244 which carries a lower roller guide or Y-axis roller guide 246, and an upper roller guide or X-axis roller guide 248.

Lower roller guide 246 and upper roller guide 248 ride within a Y-axis guideway 250 mounted substantially centrally in Y-axis plate 252, or plate No. 3, or No. 3 plate, and X-axis guideway 254, mounted in X-axis plate 256, or plate No. 4, or No. 4 plate, respectively. Plate No. 3 is provided with ball bearing mounted V-shaped wheels 260, similar to wheels 228, on its upper side. Lower wheels 258, also similar to wheels 228, roll along horizontally disposed knife-edges 262 of ways 232 of plate No. 2 while upper wheels 260 engage horizontally disposed knife-edges 264 of ways 266 provided along plate No. 4.

A cut-out portion 270 is provided in plate No. 4 to enable X-Y drive motor assembly 235 to be accommodated within the space enclosed by chair bracket support means 272 and yet permit upper roller guide 248 and lower roller guide 246 to engage X-axis guideway 254 and Y-axis guideway 250 respectively.

Chair L is mounted on adjustable means 271 affixed to chair bracket support means 272. The means for supporting chair L and adjusting the positions thereof form no part of the present invention, and are shown in several of the drawings to facilitate a better understanding of the invention.

Figure 11:
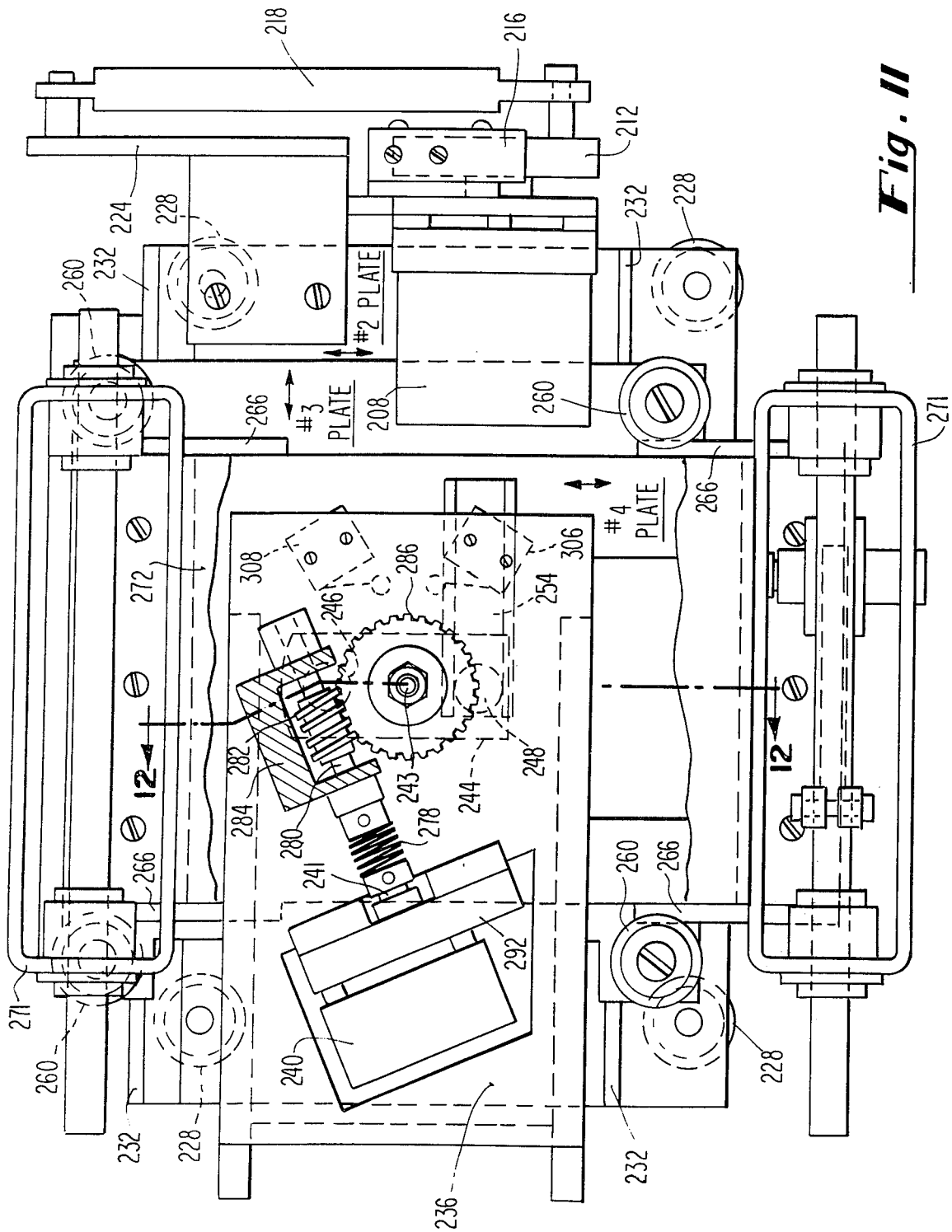
FIG. 11 is a plan view, partly in section, of the chair shift mechanism and X-Y drive mechanism of the invention with parts omitted for clarity.
Figure 12:
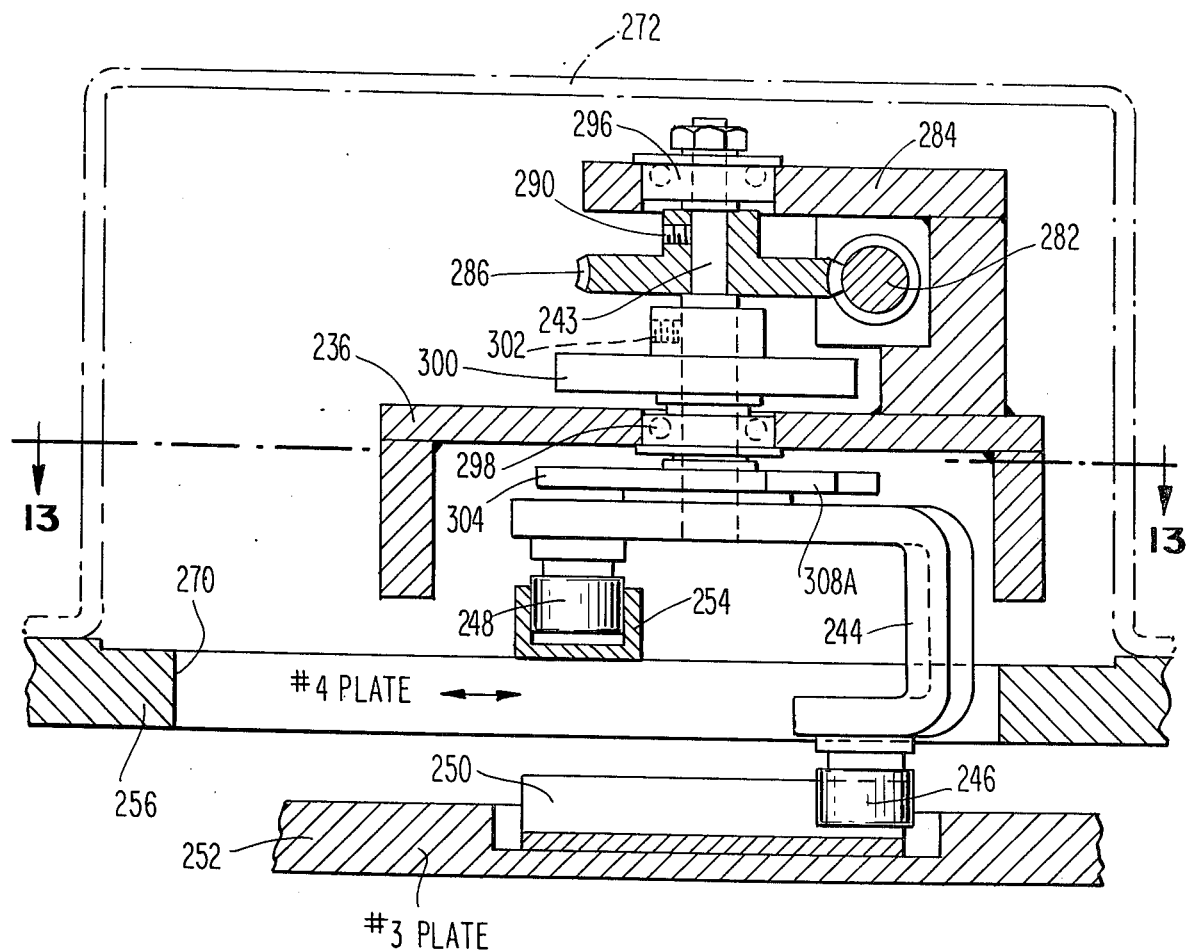
FIG. 12 is a view of the X-Y drive mechanism and gear reduction mechanism taken along line 12—12 of FIG. 11.

Referring to FIGS. 11 and 12, X-Y drive motor 240 is provided with self-aligning coupling 278 which maintains X-Y drive motor shaft 241 aligned with shaft 280 of gear reduction mechanism 242. Shaft 280 carries worm gear 282 in gear box 284. Worm gear 282 engages gear wheel 286 which is held fast to geared down shaft 243 by lock screw 290. Bracket 292, secured to mount 236, by welding, for example, maintains X-Y drive motor 240 in a fixed position. Shaft 243 is journalled into gear box 284 and mount 236 by means of bearings 296 and 298 respectively.

A disk 300 rotates with shaft 243. Disk 300 may be provided with cam lobes for actuating a microswitch assembly to increase power to the X-ray source at specified times, or a microswitch assembly may be actuated to decrease the speed of the X-ray film travel at specified times. Disk 300 is fastened to shaft 243 by lock screw 302.

A cam 304 rotates with shaft 243 for actuating a pair of reversing microswitches 306 and 308 screw mounted to an under portion of the X-Y motor mount. Cam 304 is provided with a pair of lobes 306A and 308A (FIG. 13) which limit the travel of chair transport to about 240°. More specifically, as cam 304 rotates in a counterclockwise direction, lobe 306A will actuate microswitch 306 to reverse the direction of rotation of shaft 243. Cam 304 thereupon starts rotating in a clockwise direction until lobe 308A actuates microswitch 308 to stop X-Y drive motor 240. Alternatively, actuation of microswitch 306 by lobe 306A may be used to stop X-Y drive motor 240, in order that another patient may be the treated on the return cycle of the chair to its original position. Circuitry to accomplish the above is conventional and not shown or described.

Figure 13:
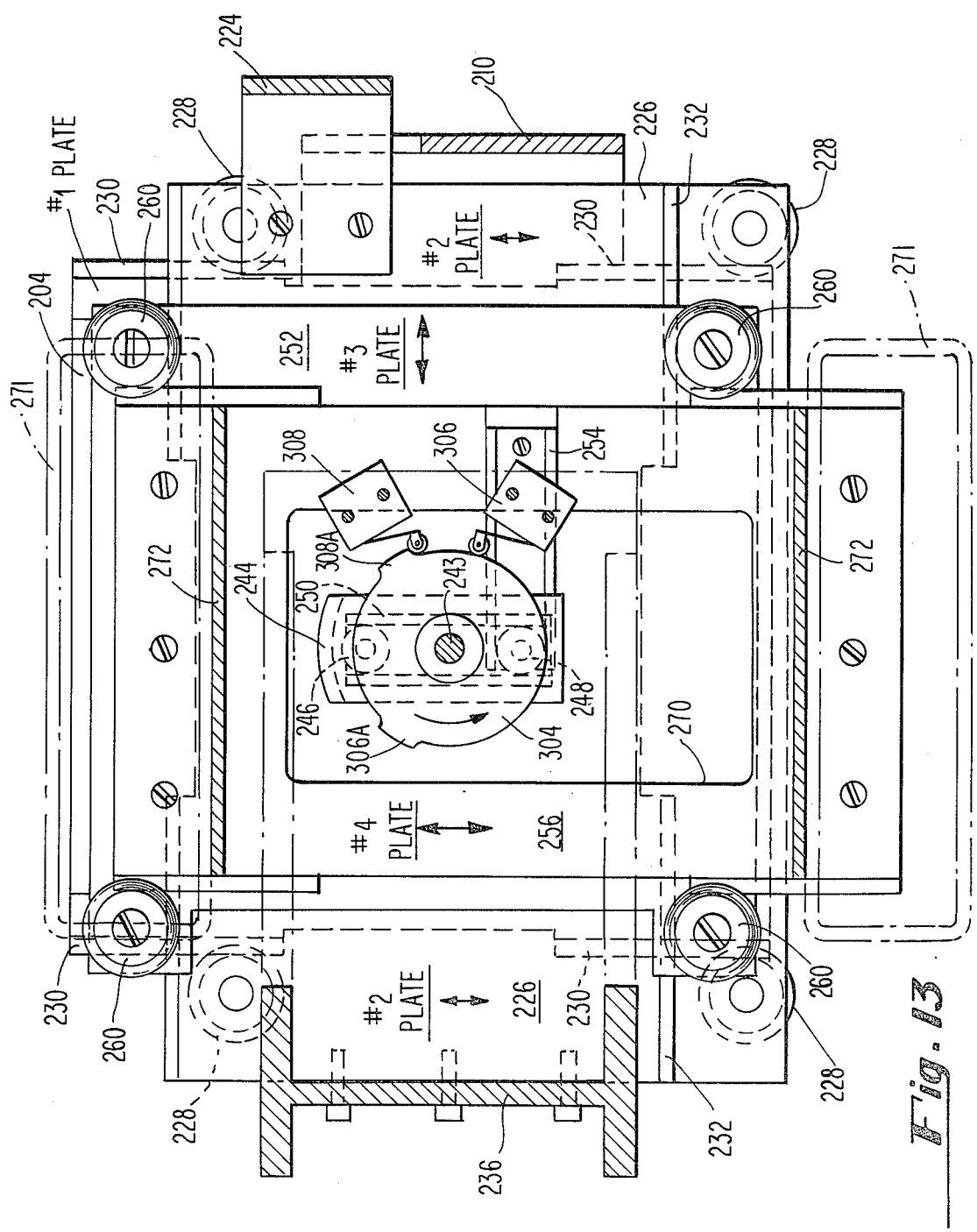
FIG. 13 is a view, partially sectioned, which, if the exploded components of FIG. 1 were assembled would have been taken substantially along a line indicated by 12—12 of FIG. 12.

FIG. 13 clearly indicates the difference in the sizes of the arcs circumscribed by the roller guides 248 and 246. That is, as crank assembly 244 rotates with shaft 243, upper roller guide 248 traces a circular path having a smaller diameter than the path traced by lower roller guide 246. This asymetrical positioning of the roller guides with respect to the axis of rotation of crank assembly 244 is essential if the chair transport pattern depicted in FIG. 14 is to be achieved.

To better understand the X-Y motion of the present panoramic dental X-ray machine, reference will now be made to FIGS. 8 and 14. In FIG. 14, upper and lower roller guides 246 and 248 are designated Y and X respectively for the sake of simplicity. Guideways 250 and 254 are similarly respectively designated.

Thus, in position designated A, chair L is at point 310, or in the $T_3$-$D_3$ position of FIG. 8. It will be appreciated that the chair is capable of transport in a counterclockwise direction 194 while the tubehead-camera assembly orbits the patient in a clockwise direction; or, as illustrated in FIG. 14, the chair may be moved in a clockwise direction in which case the tubehead-camera assembly will orbit in the opposite direction.

As the crank assembly 244 continues its counterclockwise rotation, the chair will have moved to position B, or point 312. It should be noted that the distance between the X and Y roller guides remains constant, whether in position A, B, C, D, or E, regardless of roller guide position within the respective guideways.

It should be further noted that X roller guide (upper) describes a smaller circular path than the Y roller guide (lower) as the crank assembly rotates by virtue of the X roller guide being mounted closer to the axis of rotation of shaft 243. Hence, the X roller guide will deviate from the horizontal reference line R a smaller distance than the Y roller guide.

At position C, the Y roller guide (lower) has urged the Y-axis guideway 250, and hence plate No. 3, to its farthest position from the reader, which position corresponds to position $T_2$-$D_2$ of FIG. 8. Position E corresponds with position $T_1$-$D_1$. Rotation of the crank assembly 244 in the opposite direction, or a clockwise direction, will cause the chair to follow a counterclockwise pattern as designated by the semicircular-like arc 194 of FIG. 8.

Chair L is transported from point 310 to point 314 in slightly over 20 seconds.

The distance from point 316 to point 318 is approximately 1¾ inches. The distance from point 320 to point 322 is very slightly below 1 inch.

Weight of the patient seated in chair L is distributed substantially uniformly over the upper beveled surfaces of the hardened ways which contact the hardened wheels.

Circuitry and electrical connections to achieve the objectives aforedescribed are within the skill of the art and not shown in the drawings.

Any motion of plates No. 2, 3, or 4 will be reflected in a corresponding motion of the chair. More specifically, plate No. 2 can only travel in the Y direction, or side to side, by virtue of wheels 228 of plate No. 2 engaging ways 206 of plate No. 1. The various wheels and ways; and guideways and roller guides prevent independent motion of plates No. 3 and 4 while plate No. 2 travels. That is, wheels 258 of plate No. 3 engages ways 232 of plate No. 2 and effectively prevent plate No. 3 from moving in the Y direction, or side to side. Lower roller guide 246 engages Y-axis guideway 250 of plate No. 3 to prevent its motion in the X direction, or front to back. Thus, plate No. 3 is secured against X or Y movement while plate No. 2 travels. Plate No. 4 is similarly held fast against movement while plate No. 2 travels by virtue of wheels 260 and ways 266; and upper roller guide 248 and X-axis guideway 254.

In radiographing a continuous panoramic image, plate No. 2 does not move during the travelling of plates No. 3 and 4. Drive rod 218 holds arm 224 which is rigidly mounted to plate No. 2. Thus, plate No. 2 is constrained from travelling in the Y direction. Ways 206 of plate No. 1 and wheels 228 of plate No. 2 prevent movement of plate No. 2 in the X direction.

Guideway 250 of plate No. 3 is designated the Y-axis guideway since it permits movement of lower roller guide 246 therein in a Y direction, or side to side. It should be appreciated however that plate No. 3 itself can only move in the X direction, i.e., front to back, by virture of wheels 258 engaging ways 232. Similarly, guideway 254 of plate No. 4 is designated the X-axis guideway since movement of upper roller guide 248 therein is along an X-axis, or front to back. Plate No. 4 however can only travel in the Y direction since it must move in the direction in which its ways are oriented, i.e., side to side. Chair L, however, by virtue of the mechanism aforediscussed, is capable of simultaneous movement in both the X and Y direction.

Having thus described our invention, we claim:

1. In a panoramic dental X-ray machine for providing continuous and discontinuous radiographic images of the dental arch-temporomandibular joint area of a patient seated in a chair mounted on a mechanism affixed to a stationary platform of said X-ray machine, said X-ray machine having a column carrying
    (a) a tubehead containing an X-ray source, and (b) film holder for holding film to be activated by said X-ray source,
said machine including means to power said X-ray source and means for moving said film in said film holder, and means for orbiting said column about said patient in a circular pattern, the improvement therewith wherein said mechanism comprises
    (A) means to shift said chair in a Y direction after said means to power said X-ray source and means to move said film in said film holder have been rendered inoperative during a continuous orbit of said column about said patient when said X-ray source and said film are aligned with the spine of said patient to provide a discontinuous panoramic radiographic image of said dental arch-temporomandibular joint area of said patient, and
    (B) means for transporting said chair in a semicircular-like pattern in one direction while said column continuously orbits the patient in an opposite direction to provide a continuous panoramic radiographic image of said dental arch-temporomandibular joint area of said patient, said mechanism comprising
        (a) a No. 1 plate immovably supported by said stationary platform,
        (b) a plurality of plates consisting of a No. 2 plate, a No. 3 plate, and a No. 4 plate disposed in spaced vertical relationship above said No. 1 plate, each of said plurality of plates being movable in a different direction with respect to the movable plate immediately therebeneath, (c) means attached to each of said plates for permitting movement of each of said plurality of movable plates, (d) guideway means affixed to an upper portion of plate No. 3 and plate No. 4, (e) a crank assembly having roller guide means engaging said guideway means, (f) means to rotate said crank assembly whereby said roller guide means engaged in respective guideway means urges plate No. 3 to travel in an X direction and plate No. 4 to travel in a Y direction, said travelling of plate No. 3 and plate No. 4 occurring simultaneously to yield a combined motion to said chair characterized by both X and Y directions, and (g) chair shift means for urging plate No. 2 to move in a Y direction independently of movement of plate No. 3 and plate No. 4 to move said chair attached to said mechanism in a Y direction.

2. X-ray machine as in claim 1 wherein said chair shift means comprises a pair of spaced parallel ways disposed at opposite sides of said No. 1 plate, a plurality of wheels attached to the lower side of said No. 2 plate for engaging said ways of said No. 1 plate, and means for urging said No. 2 plate to move in a Y direction when said wheels are caused to roll along said ways.

3. X-ray machine as in claim 2 comprising hardened ways having horizontally disposed knife edges, and wherein said wheels are ball bearing mounted and V-shaped, said V of said wheels mating with said knife edges when said wheels roll along said ways.

4. X-ray machine as in claim 3 wherein said means for urging said No. 2 plate to move in a Y direction comprises, a motor mounted to said No. 1 plate, said motor having an output shaft, a cam rotating in response to said shaft, an arm fixedly mounted to said No. 2 plate, a drive rod having one end off-centrally pivotally mounted to said cam and its other end connected to said arm whereby rotation of said cam causes said No. 2 plate to move in a Y direction on said V-shaped wheels and hardened ways.

5. X-ray machine as in claim 4 wherein said cam is symmetrical having a pair of opposed lobes disposed 180° apart.

6. X-ray machine as in claim 1 wherein said means for transporting said chair comprises, a pair of spaced parallel ways disposed at opposite sides of said No. 2 plate, said ways oriented along an X-axis, a plurality of wheels attached to the lower side of said No. 3 plate for engaging said ways of said No. 2 plate for permitting movement of said No. 3 plate in an X direction.

7. X-ray machine as in claim 1 wherein said means for transporting said chair comprises, a pair of spaced parallel ways disposed at opposite sides of said No. 4 plate, said ways oriented along a Y-axis, a plurality of wheels attached to the upper side of said No. 3 plate for engaging said ways of said No. 4 plate for permitting movement of said No. 4 plate in a Y direction.

8. X-ray machine as in claim 1 wherein said means for transporting said chair comprises, a pair of spaced parallel ways disposed at opposite sides of said No. 2 plate, said ways oriented along an X-axis, a pair of spaced parallel ways disposed at opposite sides of said No. 4 plate, said ways oriented along a Y-axis, a plurality of wheels attached to the lower side of said No. 3 plate for engaging said ways of said No. 2 plate and a plurality of wheels attached to the upper side of said No. 3 plate for engaging said ways of said No. 4 plate for providing a simultaneous and combined X and Y motion to said chair.

9. X-ray machine as in claim 8 further characterized by, a motor mount supported on said No. 2 plate, a crank assembly mounted on said motor mount rotating in response to said motor rotating shaft, said crank assembly including a pair of depending roller guides disposed in different planes, each of said roller guides describing an arc of revolution of different radii when rotated about an axis of rotation of said crank assembly, a guideway affixed to said No. 4 plate along an X-axis, a guideway affixed to said No. 3 plate along a Y-axis, one of said roller guides engaging said guideway affixed to said No. 4 plate and the other of said roller guides engaging said guideway affixed to said No. 3 plate, said roller guides engaged in respective guideways to urge plates to travel simultaneously in their respective directions upon rotation of said crank assembly to transport said chair in a combined X and Y direction.

10. X-ray machine as in claim 9 wherein said roller guides comprise an upper roller guide engaging said guideway disposed along an X-axis and a lower roller guide engaging said guideway disposed along a Y-axis, said upper and lower roller guides being disposed 180° apart along a horizontal axis of said crank assembly.

11. X-ray machine as in claim 9 wherein said motor rotating shaft cooperates with gear reducing mechanism mounted on said motor mount, said gear reducing mechanism providing a geared down shaft rotating at a speed slower than said motor rotating shaft, said geared down shaft driving said crank assebmly, a cam affixed to said geared down shaft for actuating means to change direction of rotation of said geared down shaft to return said chair to its original position.

12. X-ray machine as in claim 9 wherein said roller guides comprise an upper roller guide engaging said guideway disposed along an X-axis and a lower roller guide engaging said guideway disposed along a Y-axis, said upper and lower roller guides being disposed 180° apart along a horizontal axis of said crank assembly.

13. In a panoramic dental X-ray machine for providing continuous radiographic images of the dental arch-temporomandibular joint area of a patient seated in a chair mounted on a mechansim affixed to a stationary platform of said X-ray machine, said X-ray machine having a column carrying, (a) a tubehead containing an X-ray source, and (b) film holder for holding film to be activated by said X-ray source, said machine including means to power said X-ray source and means for moving said film in said film in said holder, and means for rotating said column about said patient in a circular pattern, the improvement therewith wherein said mechanism comprises means for transporting said chair in a semicircular pattern in one direction while said column continuously orbits the patient in an opposite direction to provide a continuous panoramic radiographic image of said dental arch-temporomandibular joint area of said patient, said mechanism comprising, a Y-axis plate having a channel-shaped guideway affixed thereto disposed along a Y-axis, an X-axis plate having a channel-shaped guideway affixed thereto disposed along an X-axis, means external said Y-axis plate for rotating a crank assembly, said crank assembly comprising a pair of depending roller guides disposed in different planes, each of said roller guides describing an arc of revolution of different radii when rotated about an axis of rotation of said crank assembly, one of said roller guides engaging said guideway disposed along a Y-axis and the other of said roller guides engaging said guideway disposed along an X-axis, means affixed to said Y-axis plate and X-axis plate for permitting X direction motion to said Y-axis plate and Y direction motion to said X-axis plate, said X-axis plate being in superposed relationship to said Y-axis plate, said roller guides engaged in respective guideways urging said plates to travel simultaneously in their respective directions upon rotation of said crank assembly whereby said chair is transported in accordance with a predetermined pattern.

* * * * *